United States Patent [19]
Fang

[11] Patent Number: 5,994,581
[45] Date of Patent: Nov. 30, 1999

[54] CARNITINE CREATINATE

[75] Inventor: Sen-Maw Fang, North Salt Lake, Utah

[73] Assignee: AMT Labs, Inc., North Salt Lake City, Utah

[21] Appl. No.: 09/036,854

[22] Filed: Mar. 9, 1998

[51] Int. Cl.[6] .............................................. C07C 229/26
[52] U.S. Cl. ........................................ 562/560; 562/567
[58] Field of Search ..................................... 562/560, 567; 514/554, 556

[56] References Cited

U.S. PATENT DOCUMENTS 5,030,657   7/1991   Burtle et al. .

OTHER PUBLICATIONS

Database CAPLUS on STN, Acc. No. 1970:404187, Nordmann et al., 'Antifatigue phosphocreatine salts.' GB 1185882 (abstract), 1970.
P R Borum, "Carnitine," *Ann. Rev. Nutr.* 3:233–259, 1983.
G Brevetti, et al. "Increases in Walking Distance in Patients with Peripheral Vascular Disease Treated with L–Carnitine: A Double–Blind, Cross–Over Study," *Circulation*, 77(4): 767–773, 1988.
H P Broquist, "Carnitine: A Twentieth Century Study," *FASEB Journal*, 11(3): 2088, 1997.
P Cerretelli and C Marconi, "L–Carnitine Supplementation in Humans. The Effects on Physical Performance," *Int. J. Sports Med.* 11: 1–4, 1990.
R N Cortright, D M Muoio, and G L Dohm, "Skeletal Muscle Lipid Metabolism: A Frontier for New Insights into Fuel Homeostasis," *Nutritional Biochemistry*, 8: 228–245, 1997.
J R Dipalma, "L–Carnitine: Its Therapeutic Potential," *American Family Physician*, 34(6): 127–130, 1986.
J R Dipalma, "Carnitine Deficiency," *American Family Physician*, 38(1): 243–251, 1988.
R Ferrari, F Cucchini and O Visioli, "The Metabolical Effects of L–Carnitine in Angina Pectoris," *Int'l J of Cardiology*, 5: 213–216, 1984.
J D Folts, A L Shug, J R Koke, N Bittar, "Protection of the Ischemic Dog Myocardium with Carnitine," *American J. of Cardiology*, 44:1209–1214, 1978.
E M Gorostiaga, C A Maurer, J P Eclache, "Decrease in Respiratory Quotient during Exercise Following L–Carnitine Supplementation," *Int. J. Sports Med.*, 10: 169–174, 1989.
S Hirose, et al., "Carnitine Depletion during Total Parenteral Nutrition Despite Oral L–Carnitine Supplementation," *Acta Paediatrica Japonica*, 39: 194–200, 1997.

T Kamikawa et al., "Effects of L–Carnitine on Exercise Tolerance in Patients with Stable Angina Pectoris," *Japanese Heart Journal*, 25: 587–597, 1984.
S Keskin, A Seven, M Mert, F Akalp, F Yurdakul, and G Candan, "Could L–Carnitine be an Acute Energy Inducer in Catabolic Conditions?", *Dev Med Child Neurol* 39(3): 174–177, 1997.
K Lim, S Choi, Y S Cha, and D S Sachan, "Carnitine and Caffeine Administration Increases Fat Oxidation and Endurance Performance in Athletes," *FASEB J.*, 11(3): 2174, 1997.
C Miki, K Iriyama, B K Gunson, H Suzuki and P McMaster, "Plasma Carnitine Kinetics during Orthotopic Liver Transplantation," *Scand J Gastroenterol*, 32(4): 357–362, 1997.
CJ Rebouche, DJ Paulson, "Carnitine Metabolism and Function in Humans," *Ann.Rev. Nutr.* 6:41–66, 1986.
A A–Shurbaji et al., "On the Interrelationship between Hepatic Carnitine, Fatty Acid Oxidation, and Triglyceride Biosynthesis in Nephrosis," *Lipids*, 32(8) 847–852, 1997.
L Vecchiet et al., "Influence of L–Carnitine Administration on Maximal Physical Exercise," *Eur J Appl Physiol*, 61: 486–490, 1990.
Sigma–Tau Pharmaceuticals, Inc., "Carnitor," *Physicians Desk Reference*, pp. 2623–2625, 1997.

*Primary Examiner*—Gary Geist
*Assistant Examiner*—Brian J. Davis
*Attorney, Agent, or Firm*—Thorpe North & Western, LLP

[57] ABSTRACT

The present invention relates to the formation of a salt between carnitine and creatine which has unique and useful attributes over creatine monohydrate or carnitine base. An acid-base reaction between carnitine and creatine causes the formation of the salt composition. Further, the invention provides a salt form of carnitine which is very stable and non-hygroscopic. The carnitine creatinate product of the present invention is represented by the following:

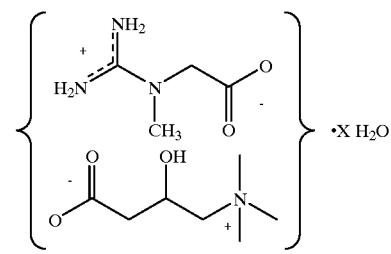

wherein X is an integer between about 0 and 5.

6 Claims, No Drawings

CARNITINE CREATINATE

BRIEF DESCRIPTION OF THE INVENTION

This invention relates to the formation of a salt between carnitine and creatine which has unique and useful attributes over creatine monohydrate or carnitine base. More specifically, this invention relates to a carnitine creatinate salt that provides a significantly improved taste over carnitine salts, such as tartrate and citrate, heretofore available. Additionally, it provides a salt form of carnitine which is very stable and non-hygroscopic. The combined compound is an excellent choice in diet formulations because it improves metabolic fat burning and provides an extra energy boost.

BACKGROUND OF THE INVENTION

Creatine, also known as N-(Aminoiminomethyl)-N-methylglycine, methylglycoamine or N-methyl-guanido acetic acid is listed in the MERCK INDEX, an accepted chemical encyclopedia and may be represented by the following depiction:

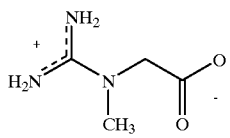

(*The Merck Index* Tenth Edition, No. 2551). Perhaps, because of the positioning of the —$NH_2$ group gamma to the carboxylic acid, creatine is labile to acid hydrolysis. Regardless, however, of any purported rational, creatine is susceptible to cyclization under acid conditions to form creatinine which may be represented by the following depiction:

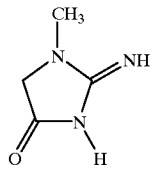

In acidic aqueous solutions the formation of creatinine from creatine is nearly quantitative and irreversible (Cannan, Shore, *Biochem. J.* 22, 924: 1928). Creatinine is, as well, one by-product of normal metabolic use of creatine and has been used as a diagnostic marker of such use. Moreover the exposure of creatine to the acidic environment of the gut would be expected to cause the irreversible formation of creatinine precluding further biological use of ingested creatine. Furthermore, the ingestion of creatine has been associated with marked stomach and gastric upset. Although the ingestion of creatine and gastric upset are perhaps only linked by empirical observation, the acid stability of creatine and subsequent formation of creatinine provide potential reasons.

Muscle contraction and relaxation are fueled by the free energy liberated by the dephosphorylation of adenosine triphosphate (ATP). The ATP stored within cells is rapidly depleted during even normal activity. For normal tissue function to continue, ATP must be rapidly resynthesized from its breakdown products, one of which is adenosine diphosphate (ADP). During maximal exercise of a short duration this resynthesis is accomplished almost exclusively by the anaerobic degradation of phosphocreatine (PCR) and glycogen (Hultman E. et al.; *Energy metabolism and fatigue.* In: Taylor A, Gollnick P, Green H, et al., eds. *Biochemistry of Exercise* VII. Champaign, Ill: Human Kinetic Publishers, 1990: vol. 21, 73–92). Greenhaff et al. proposed that the observed decline in force production during intense contraction may be related to the availability of muscle PCR stores (Greenhaff P. L., Casey A., Short A. H., Harris R., Soderlund K., Hultman E.; *Influence of oral creatine supplementation of muscle torque during repeated bouts of maximal voluntary exercise in man; Clinical Science* (1993) 84,565–571). The depletion of these PCR stores limits the rephosphorylation of ADP, thereby limiting the ATP available for energy production. Greenhaff et al. further proposed that any mechanism capable of increasing the intramuscular total creatine store might arrest PCR depletion during intense muscular contraction and offset or even prevent the decline in the rate of ADP rephosphorylation during exercise. Greenhaff et al. did not document means whereby the effective amount of creatine within the muscle cells could be increased. Indeed, Greenhaff et al. relied upon work previously published by Harris et al. where it was demonstrated that the creatine content of skeletal muscles may be increased, however by only 20–50%, through standard oral pathways. Importantly, in order to achieve this mediocre increase in the creatine content of muscle cells the subjects of the study were required to ingest 20 grams of creatine monohydrate, much of which was washed out through the urine instead of being assimilated and metabolized (Harris RC, Soderlund K, Hultman E.; *Elevation of creatine in resting and exercised muscle of normal subjects by creatine supplementation., Clin. Sci.,* 1992; 83: 367–74).

Creatine can be found biologically in many forms and in diverse portions of the body. Walker reports creatine to exist mainly in the nerves and muscle (Walker J.B.; *Creatine: Biosynthesis. regulation, and function Adv. Enzymology and Related Areas of Molecular Biology* (1979) 50: 177–242). Creatine has a normal turnover rate of about 2 grams per day. The biochemical process which uses creatine for the regeneration of ATP from ADP irreversibly transforms creatine to creatinine which is eliminated through the urine. Because creatine is irreversibly used, the body must either produce creatine biochemically or secure an adequate outside source.

Biochemically creatine is synthesized in the human liver and pancreas whereas creatine is synthesized exclusively in the liver by members of the poultry family. The human liver and pancreas use the amino acids glycine, serine, arginine and methionine to synthesize creatine. However, where sufficient creatine is made bioavailable through ingestion such biosynthesis would seem unnecessary. Although animal muscle contains approximately 0.5% creatine by weight, most of this is degraded by cooking thereby precluding cooked meat from the potential list of external sources of ingestible bioavailable creatine. Moreover, neither plant nor vegetable matter provides a source of creatine.

Creatine has been a component in several recent U.S. patents. U.S. Pat. No. 5,397,786 entitled REHYDRATION DRINK discloses and claims a rehydration drink for the treatment and prevention of the loss of essential electrolytes because of fluid loss. This patent teaches that creatine, B vitamins, pantothenic acid and choline are energy enhancers. Additionally, this invention suggests the addition of numerous salts such as $MgCO_3$, $CaCO_3$ and magnesium aspartate as supplements which contain essential nutrients for healthy metabolism. However, the use of ionic salts such as $MgCO_3$ is less effective than desired because most of the ingested element is lost in the acidic environment of the gut.

U.S. Pat. No. 5,576,316 entitled METHOD FOR INHIBITING TUMOR GROWTH RATE USING CREATINE OR CREATINE ANALOGS issued Nov. 19, 1996. This patent teaches the use of creatine and creatine analogs for the treatment of tumors. Specifically this invention teaches that the administration of creatine in the form of a salt can reduce a tumor's growth rate. Importantly, this patent also teaches that significant portions of orally administered creatine are lost through the urine without having been used by the host Although the potential causes for this observance are not stated, one reason could be the low solubility of creatine in water to account for the observed preclusion of ingested creatine from biological use.

Carnitine (3-Carboxy-2-hydroxypropyl) trimethylammnonium hydroxide inner salt (CAR) may be represented graphically according to the depiction of Graphic I.

Graphic I

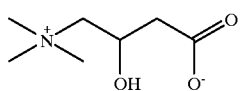

There are two chemical forms of CAR, L-CAR and D-CAR, of which L-CAR is biologically active and is pharmaceutically available for medicinal indications. Biologically, a portion of CAR binds fatty acids forming acyl (A) CAR while the rest exists as free (F) CAR. The sum of these two fractions is referred to as total (T) CAR Some of its physiological roles in fatty acid oxidation and in the excretion of organic acids have been well investigated.

L-Carnitine functions as a carrier molecule in the transport of long chain fatty acids across the inner mitochondrial membrane. It delivers substrate for oxidation and subsequent energy production.

Carnitine's essential role is to transport fatty acids of 12–18 carbons across the outer and inner membranes of the mitochondria. Carnitine palmitoyltransferase catalyzes the transfer of the fatty acid or acyl group to carnitine at the outer surface of the mitochondrial membrane. The acylcarnitine then goes across the outer membrane of the inner surface of the mitochondrial membrane. Here the acyl group is transferred back to coenzyme A under the influence of carnitine palmitoyltransferase II (*Carnitine Deficiency* Dipalma J. R., *American Family Physician*, 38 (1): 243–251, 1988).

L-Carnitine is used in the treatment of primary systemic carnitine deficiency. Clinical presentation can include recurrent episodes of Reye-like encephalopathy, hypoketotic hypoglycemia, and/or cardiomyopathy. Other associated symptoms included hypotonia, muscle weakness, and failure to thrive (*Physicians Desk Reference*, 1997, p. 2624).

L-Carnitine may also alleviate the metabolic abnormalities of patients with inborn errors of metabolism that result in the accumulation of toxic organic acids (*Physicians Desk Reference*, 1997, p.2623).

Carnitine's importance in cardiac metabolism and function has been emphasized by a number of studies showing a close association between systemic and myopathic carnitine deficiency and both hypertrophic and congestive cardiomyopathies (*Carnitine Metabolism and Function in Humans.* Rebouche C. J., Paulson D. J., *Ann Rev* 1986. 6: 41–66).

Reports indicate L-Carnitine therapy converts abnormal fatty acid metabolism to normal, increases the concentration of L-Carnitine in cardiac muscle and in blood, and improves cardiac output and blood pressure (*L-Carnitine: Its Therapeutic Potential.* Dipalma J. R. *Amer Fam Phys* 34(6): 127–130, 1986).

L-Carnitine may improve exercise tolerance in patients with effort angina (*Effects of L-Carnitine on Exercise Tolerance in Patients with Stable Angina Pectoris. Japanese Heart Journal* 25: 587, Karikawa T. et al., 1984). L-Carnitine converted lactate production to extraction and increased the percentage of free fatty acid extraction, suggesting a use to improve the metabolism of coronary artery disease patients (*The Metabolical Effects of L-Carnitine in Angina Pectoris.* Ferrari R., Cucchini F., Visioli O., *International Journal of Cardiology* 5(1984): 213–216). L-Carnitine has also improved the walking capacity of patients with intermittent claudication (*Increases in Walking Distance in Patients with Peripheral Vascular Disease Treated with L-Carnitine. A Double-Blind, Cross-Over Study.* Brevetti G., Jannelli V. G., et al. *Circulation* Vol. 77, No. 4,767–773, April 1988). L-Carnitine may benefit the ischemic myocardium by maintaining tissue levels of free carnitine (*Protection of the Ischemic Dog Myocardium with Carnitine.* Folts J. D., Shug A. L., Koke J. R., Bittar N., *American Journal of Cardiology* 41: 1209, 1978).

Patients with type II or type IV hyperlipoproteinemia, when treated with 3 grams of oral carnitine per day, had a marked reduction in serum cholesterol and serum triglyceride (*Carnitine.* Borum, P. R. *Ann Rev Nutr* 1983. 3: 233–259).

Carnitine may be an essential nutrient for the newborn (*Carnitine.* Borum, P. R. *Ann Rev Nutr* 1983. 3: 233–259). L-Carnitine has promise in reducing the fat accumulation in certain types of fatty livers (*L-Carnitine: Its Therapeutic Potential.* Dipalma J. R. *Amer Fam Phys* 34(6): 127–130, 1986). The use of L-Carnitine in dialysis patients may be important in individual cases *L-Carnitine: Its Therapeutic Potential.* Dipalma J.R. *Amer Fam Phys* 34(6): 127–130, 1986).

Meat and dairy products are the major sources of carnitine in the United States. Cereal, fruits, and vegetables contain little or no carnitine (*Carnitine.* Borum, P. R. *Ann Rev Nutr* 1983. 3: 233–259).

Individuals on enteral nutrition for long periods of time whose protein source is soy protein isolate, casein, or egg white protein get low amounts of carnitine (4 nmol/ml carnitine or less) (*Carnitine.* Borum, P. R. *Ann Rev Nutr* 1983. 3: 233–259).

There is evidence of increased $VO_2$ max with carnitine supplementation. This is probably through the removal of part of the short-chain acyl-CoA by L-Camnitine in the muscles heavily involved in exercise with a concurrent release of free CoA. This would stimulate pyruvate dehydrogenase and enhance flux in the Krebs Cycle (*L-Carnitine Supplementation in Humans. The Effects on Physical Performance.* Cerretelli P., Marconi C., *Int J. Sports Med* 11 (1990) 1–14).

L-Carnitine could be advantageous to exercising individuals, as prolonged exercise increases the urinary excretion of carnitine (*L-Carnitine Supplementation in Humans. The Effects on Physical Performance.* Cerretelli P., Marconi C., *Int J. Sports Med* 11 (1 990) 1–14).

A positive effect of L-Carnitine is an increase of muscles' anaerobic capacity. Carnitine, by functioning as an acetyl group buffer, 1) Maintains a viable pool of CoA even when the rate of acetyl-CoA formation exceeds that of condensation of the above metabolite with oxaloacetate, 2) Prevent "flooding" of the mitochondrial matrix by acetyl-CoA esters, 3) Act as an additional sink for pyruvate, and 4) Improve the transport of adenine nucleotides (*L-Carnitine Supplementation in Humans. The Effects on Physical Performance.* Cerretelli P., Marconi C., *Int J. Sports Med* 11 (1990) 1–14).

L-Carnitine may increase lipid utilization by muscle during exercise. (*Decrease in Respiratory Quotient During Exercise Following L-Carnitine Supplementation.* Gorostiaga E. M., Maurer C. A., Eclache J. P., *Int J. Sports Med.* 10 (1989) 169–174.

L-Carnitine has been shown to increase both maximal oxygen uptake and power output (*Influence of L-Carnitine Administration on Maximal Physical Exercise.* Vecchiet L., et al. *European Journal of Applied Physiology* (1990) 61: 486–490).

In the supplementation of L-CAR for patients on long-term total parenteral nutrition, especially for patients with short bowel syndrome, a more practical problem arises. Oral supplementation of L-CAR of the type known cannot provide a sufficient amount of CAR when patients have severe malabsorption, because it is not easily absorbed. For this population, intravenous supplementation is considered. However, the availability of L-CAR for intravenous administration is limited because of a lack of metabolically acceptable salts of carnitine.

Carnitine possesses an unpleasant smell and is hygroscopic as a solid. The hygroscopicity makes it very difficult to store carnitine, especially as a solid. The creatine salt of carnitine of the present invention overcomes these problems and possesses a distinct yet pleasant taste and is not hygroscopic.

OBJECTS OF THE INVENTION

It is therefore an object of the present invention to provide a salt of carnitine with creatine.

It is an additional object of the invention to provide a caraitine salt having improved palatability and decreased hygroscopicity.

It is still another object of the invention to provide a creatine salt of camitine which has improved palatability and metabolic availability.

These and other objects may be accomplished by means of an organic salt formed of creatine and carnitine and their attendant salts and ananalogue. As used herein,the term "carnitine analogue" will connote a salt or derivative of carnitine such as a member selected from the group consisting of carnitine hydrochloride, carnitine esters, carnitine amides, camitine imides and mixtures thereof. Similarly, the term "creatine analogue" will connote a substance which is made from chemical manipulation of creatine.

DETAILED DESCRIPTION OF THE INVENTION

Both creatine and camitine are bimorphic, each containing an acidic and a basic moiety. This somewhat unique dual character creates a natural analogy between creatine and carnitine, the corresponding salt formed, and analogous salts of amino acids. Amino acids also possess both acidic and basic moieties within one molecular structure. Because of this dual nature, amino acids, creatine, and carnitine may be either the anionic or the cationic portion of a salt which includes them. Specifically these dual functionality compounds can be used as either the acid or the base in the formation of a salt through an acid-base reaction. Moreover, these dual functionality organic compounds often form interior, intramolecular salts, e.g. a salt formed of its own acidic and basic portions. Carnitine is an α-hydroxy carboxylic acid and creatine is an α-N(aminoiminomethyl) carboxylic acid and the acid-base reaction between these two causes the formation of the salt composition which is one embodiment of the present invention. Importantly the properties of the salt comprising creatine and carnitine, namely carnitine creatinate, are unexpected in that the salt is more stable than the two organic moieties of which it is made and has a distinct yet pleasant taste.

Furthermore, carnitine creatinate salt of the present invention is a unique chemical composition as evidenced by the designation of a Chemical Abstracts Service unique identifer. This unique identifer is given to new chemical compositions by the Chemical Abstracts Service (CAS). The unique CAS number assigned the unique carnitine creatinate chemical composition of the present invention is 201790-31-0.

PREFERRED EMBODIMENT AND EXAMPLES

A preferred embodiment of the present invention would be prepared according to the following:

EXAMPLE 1

One mole of camitine (161.20 grams) is mixed with one mole of creatine monohydrate (149.15 grams) in a 4:1 w:w mixture of isopropanol (40 g):water (10 g). The mixture is heated to 70–72° C. until the mixture becomes a soft mass. Continued mixing for an additional 5 minutes with subsequent cooling to 15–20° C. results in a solid material. The solid is further dried at reduced pressure (400–500 mm Hg) at no higher than 45° C. The resultant carnitine creatinate monohydrate salt has a molecular weight of 310.35 with a decomposition melting point of 184–188° C. and is a non-hygroscopic solid with a distinct yet agreeable taste.

The salt synthesized according to this example can be administered in daily dosages of between about 50 and 2,000 mg/day. Such dosages can be in a single dose or in divided, multiple doses. The salt can be pressed into tablets, placed in capsules, formulated as a syrup or elixir, or prepared by any other conventional mechanism for oral dosage. Preferably, because of its improved palatability, the salt in powder form can be administered by dispersing or dissolving it in a drink such as fruit juice. It may also be combined with protein powders or other food sources designed to improve metabolic performance.

EXAMPLE 2

A panel of ten people were given samples of a mixture of 100 mg of creatine monohydrate and 100 mg of carnitine in 250 ml of apple juice. The same panel was given 200 mg carnitine creatinate formed in Example 1 in 250 ml of apple juice. The samples were merely labeled A and B and each member of the panel was free to elect which sample to taste first. In all instances the sample containing the carnitine creatinate salt was judged to have the better taste.

EXAMPLE 3

The resultant carnitine creatinate salt, in solid form from Example 1, in dosages of from about 50 to 2000 mg, can be mixed with 8 oz. water or juice and taken as an exercise supplement This supplement can be taken in single or divided doses such that between 50 mg to 2000 mg of the carnitine creatinate salt is ingested each 24 hour period.

While the above example shows a 1:1 molar ratio of creatine to carnitine to form a salt, the molar ratio may vary from between about 0.1:1 to 1:0.1 creatine to carnitine. This may be accomplished because creatine and carnitine form stable salts internally. Indeed, one of skill in the art would understand the various ratios and manners in which these two organic compounds may be advantageously combined.

In summary, it is to be noted that creatine is an important factor in the regeneration of ATP. Carnitine is an essential cofactor for many metabolic interactions in the body particularly in the role of fatty acid oxidation and in the excretion of organic acids. Both creatine and carnitine have a characteristic unpleasant taste when administered orally. Moreover, creatine monohydrate is only slightly water soluble. Additionally inorganic and internal salts of carnitine are unstable and hygroscopic. The carnitine creatinate salt of the present invention greatly improves palatability and overall stability and enables the optimal biofunctionality of both creatine and carnitine in enhancing energy and metabolic rates.

Furthermore, significant publications and research have concluded that nitrogen metabolism and growth are promoted by CAR ingestion, with some studies concluding that CAR injection should be a part of normal TPN, especially for pediatric patients. However, the instability and marked hygroscopicity of carnitine has made such use difficult The present invention ameliorates this and other concerns by providing a carnitine salt which is stable and non hygroscopic. Moreover the salt of the present invention accomplishes this benefit while providing the unexpected additive advantage of assisting in muscle energy stores.

Therefore, the salt of the present invention is more beneficial than a simple mixture of inorganic salts of carnitine and creatine because the carnitine creatinate salt of the present invention is nonhygroscopic. Furthermore, the present invention provides for improved palatability and would be better accepted by the user.

What is claimed is:

1. A salt of a creatine member and a carnitine member wherein the molar ratio between the creatine member and the carnitine member is between about 0.1:1 to 1:0.1.

2. The salt according to claim 1 wherein the creatine member is selected from the group consisting of creatine, creatine esters, creatine amides, creatine imides, and mixtures thereof.

3. The salt according to claim 2 wherein the carnitine member is selected from the group consisting of carnitine, carnitine esters, carnitine amides, carnitine imides, carnitine ammonium salts, and mixtures thereof.

4. The salt according to claim 2 wherein the creatine member is creatine.

5. The salt according to claim 4 wherein the carnitine member is carnitine.

6. The salt according to claim 5 being represented by the formula:

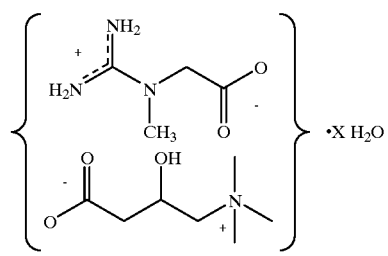

wherein X is an integer between about 0 and 5.

* * * * *